(12) United States Patent
Foo et al.

(10) Patent No.: US 10,806,947 B2
(45) Date of Patent: Oct. 20, 2020

(54) METHODS AND SYSTEMS TO DETERMINE RESPIRATORY PHASE AND MOTION STATE DURING GUIDED RADIATION THERAPY

(71) Applicant: GENERAL ELECTRIC COMPANY, Schenectady, NY (US)

(72) Inventors: Thomas Kwok-Fah Foo, Clifton Park, NY (US); Lowell Scott Smith, Niskayuna, NY (US); Kai Erik Thomenius, Clifton Park, NY (US); Sandeep Narendra Gupta, Clifton Park, NY (US); Luca Marinelli, Niskayuna, NY (US); Kedar Anil Patwardhan, Maharashtra (IN); Dominic Michael Graziani, Loudonville, NY (US)

(73) Assignee: General Electric Company, Schenectady, NY (US)

( * ) Notice: Subject to any disclaimer, the term of this patent is extended or adjusted under 35 U.S.C. 154(b) by 417 days.

(21) Appl. No.: 15/277,198

(22) Filed: Sep. 27, 2016

(65) Prior Publication Data

US 2017/0014645 A1 Jan. 19, 2017

Related U.S. Application Data

(63) Continuation-in-part of application No. 13/797,395, filed on Mar. 12, 2013, now abandoned.

(51) Int. Cl.
*A61B 5/00* (2006.01)
*A61N 5/10* (2006.01)
(Continued)

(52) U.S. Cl.
CPC .......... *A61N 5/1049* (2013.01); *A61B 5/0035* (2013.01); *A61B 5/055* (2013.01);
(Continued)

(58) Field of Classification Search
CPC .................................................. A61B 8/5261
See application file for complete search history.

(56) References Cited

U.S. PATENT DOCUMENTS

2004/0097805 A1* 5/2004 Verard ............... A61B 1/00071
600/428
2004/0106869 A1* 6/2004 Tepper ................. A61B 8/0833
600/443
(Continued)

OTHER PUBLICATIONS

Medical Imaging and Augmented Reality, 4th International Workshop, 2008. Has a chapter on "Real-Time Autostereoscopic Visualization of Registration-Generated 4D MR Image of Beating Heart" p. 349. (Year: 2008).*
(Continued)

*Primary Examiner* — Joanne M Hoffman

(57) ABSTRACT

Methods and systems using magnetic resonance and ultrasound for tracking anatomical targets for radiation therapy guidance are provided. One system includes a patient transport configured to move a patient between and into a magnetic resonance (MR) system and a radiation therapy (RT) system. An ultrasound transducer is also provided that is hands-free and electronically steerable, securely attached to the patient, such that the ultrasound transducer is configured to acquire four-dimensional (4D) ultrasound images concurrently with one of an MR acquisition or an RT radiation therapy session. The system also includes a controller having a processor configured to use the 4D ultrasound images and MR images from the MR system to control at least one of a photon beam spatial distribution or intensity modulation generated by the RT system. The system determines the previously-acquired correct MR images that represent a specific motion state at some time, t, by a plurality of transformations that allow the representation of the position of fiducial markers in the correspond-
(Continued)

ing ultrasound images to match that of a prior ultrasound acquisition.

9 Claims, 8 Drawing Sheets

(51) Int. Cl.
  *A61B 5/055* (2006.01)
  *A61B 8/08* (2006.01)
  *A61B 5/113* (2006.01)
(52) U.S. Cl.
  CPC .............. *A61B 5/113* (2013.01); *A61B 8/085* (2013.01); *A61B 8/483* (2013.01); *A61B 8/5215* (2013.01); *A61N 5/1037* (2013.01); *A61B 5/0555* (2013.01); *A61N 5/1067* (2013.01); *A61N 2005/1055* (2013.01); *A61N 2005/1058* (2013.01); *A61N 2005/1063* (2013.01)

(56) References Cited

U.S. PATENT DOCUMENTS

| | | | | |
|---|---|---|---|---|
| 2005/0259864 | A1* | 11/2005 | Dickinson | G06K 9/00134 382/154 |
| 2006/0241443 | A1* | 10/2006 | Whitmore, III | A61B 8/08 600/439 |
| 2007/0003118 | A1* | 1/2007 | Wheeler | G06T 7/001 382/128 |
| 2007/0015991 | A1* | 1/2007 | Fu | A61B 8/08 600/407 |
| 2007/0167705 | A1* | 7/2007 | Chiang | A61B 5/6805 600/407 |
| 2007/0280556 | A1* | 12/2007 | Mullick | G06T 5/50 382/294 |
| 2009/0054772 | A1* | 2/2009 | Lin | A61N 7/02 600/439 |
| 2009/0097723 | A1* | 4/2009 | Washburn | A61B 8/06 382/128 |
| 2009/0097778 | A1* | 4/2009 | Washburn | A61B 90/36 382/294 |
| 2010/0054630 | A1* | 3/2010 | Avinash | G06F 3/04845 382/294 |
| 2011/0160566 | A1* | 6/2011 | Petropoulos | A61N 5/1049 600/411 |
| 2012/0035462 | A1* | 2/2012 | Maurer, Jr. | A61B 6/5247 600/411 |
| 2012/0321195 | A1* | 12/2012 | Jhunjhunwala | G06T 7/33 382/195 |
| 2013/0261429 | A1* | 10/2013 | Lee | A61B 5/055 600/411 |
| 2013/0345545 | A1* | 12/2013 | Gross | A61B 5/055 600/411 |

OTHER PUBLICATIONS

Q. Zhang, X. Huang, R. Eagleson, G. Guiraudon, T. M. Peters, "Real-time dynamic display of registered 4D cardiac MR and ultrasound images using a GPU," Proc. SPIE 6509, Medical Imaging 2007: Visualization and ImageGuided Procedures, 65092D (Mar. 22, 2007) (Year: 2007).*

Porter, "Three-Dimensional Registration and Fusion of Ultrasound and MRI Using Major Vessels as Fiducial Markers", IEEE Transactions on Medical Imaging, vol. 20, No. 4, Apr. 2001 (Year: 2001).*

Curiel, "Progress in Multimodality Imaging: Truly Simultaneous Ultrasound and Magnetic Resonance Imaging", 2007, IEEE Trans Med Imaging, 26(12), pp. 1-17 (Year: 2007).*

* cited by examiner

METHODS AND SYSTEMS TO DETERMINE RESPIRATORY PHASE AND MOTION STATE DURING GUIDED RADIATION THERAPY

CROSS REFERENCE TO RELATED APPLICATIONS

This application is a continuation-in-part of U.S. Nonprovisional patent application Ser. No. 13/797,395, entitled "Methods and Systems Using Magnetic Resonance and Ultrasound for Tracking Anatomical Targets for Radiation Therapy Guidance", filed Mar. 12, 2013, which is herein incorporated.

BACKGROUND

In radiation therapy, the planning treatment volume (PTV) is usually set to be much larger than the clinical tumor volume (CTV). This is due to the fact that during respiration, the tumor target can move (e.g., as much as 3 centimeters (cm)).

Typically, the PTV is set to be much larger than that of the CTV in order to provide effective dose delivery to the tumor. With respect to the gross tumor volume (GTV), CTV, internal target volume (ITV), and PTV, GTV is less than CTV, PTV. In conventional systems, the CTV defines the target volume that includes a margin to account for complete treatment of the tumor based on physiological information and also on clinical treatment experience. Moreover, the ITV is typically set much larger than the CTV to account for uncertainties in the disposition of the anatomy, such as from respiration. When perform radiation therapy, the PTV is set to the volume to deliver the prescribed radiation dose to the CTV accounting for the different beam treatment angles and also the different geometries.

Accordingly, in conventional systems, this larger ITV region results in substantial damage to a much larger volume of healthy tissue, which can include a nearby critical organ. Thus, conventional radiation therapy systems have this undesirable side-effect, with the collateral damage to healthy tissue having an even greater impact when critical organs are in proximity to the tumor volume. An example of this adverse effect is in the treatment of prostate cancer where the colon, bladder and rectum may not be involved in the treatment, but may suffer significant radiation damage from the therapy. This radiation damage can result in loss of normal function of the organs and can negatively affect the quality of life.

Real-time guidance is desirable to either "gate" the radiation beam such that it is switched off when the tumor target moves away from the treatment volume that was already pre-prescribed or the PTV is dynamically altered during the treatment in response to the physical movement and deformation (if any) of the tumor volume.

There are a number of known systems and methods that include integrating x-ray computed tomography (CT) with a linear accelerator (LINAC), the device that delivers the radiation dose. There are also other known systems and methods that integrate a LINAC with an MR scanner. However, all these conventional approaches have disadvantages of increased radiation dose to healthy tissue, poor soft tissue and tumor margin delineation, and/or have significant technological challenges or cost, for example the combination of a LINAC and MR scanner. Therefore, a need exists to determine the determine the position of a tumor target or treatment volume in response to physical movement and deformation. In addition, the determination of position would beneficially take into account physical movement or deformation of the tumor target or treatment volume as attributed to autonomous nervous system function such as respiration.

BRIEF DESCRIPTION

In accordance with various embodiments, a system is provided that includes a patient transport configured to move a patient between and into a magnetic resonance (MR) system and a radiation therapy (RT) system and an ultrasound transducer coupled to the patient or the patient transport, wherein the ultrasound transducer is configured to acquire four-dimensional (4D) ultrasound images concurrently with an MR acquisition session and a separate RT radiation therapy session. The system also includes a controller having a processor configured to use the 4D ultrasound images and MR images from the MR system to control at least one of a photon beam spatial distribution or intensity modulation generated by the RT system. In one embodiment, specific separate patient transports may be utilized that have the same characteristic pertinent to a radiation therapy treatment (such as a flat table-top), but can operate in an MR system and an RT system.

In accordance with other various embodiments, a method for tracking anatomy for radiation therapy treatment is provided. The method includes acquiring, using an ultrasound device attached to a patient or coupled to a patient support, real-time four-dimensional (4D) ultrasound images during a treatment phase for radiation therapy and using the acquired real-time 4D ultrasound images to indirectly obtain higher spatial resolution magnetic resonance (MR) images of a tumor using 4D ultrasound images acquired during a pre-treatment phase using the ultrasound device. The higher spatial resolution MR images have a higher spatial resolution than the 4D ultrasound images; and the higher spatial resolution MR images acquired during the pre-treatment phase are correlated to the 4D ultrasound images. The method also includes controlling at least one of a photon beam spatial distribution or intensity modulation generated by a radiation therapy (RT) system using the higher spatial resolution MR images.

The method for tracking anatomy for radiation therapy treatment relies on using the MR images during radiation therapy that were acquired at a different time during the pre-treatment phase. The MR images can be used to account for physical movement such as during respiration, or deformation of the tumor target or treatment volume during respiration or other autonomous nervous system functional movement. In reference to respiratory motion, the 4D ultrasound images are used to determine the respiratory phase or the motion state of the patient, and do not register to the MR images. The ultrasound images do not utilize physical registration to the MR images to determine the respiratory or motion state, but rather the respiratory motion state for the MR images is determined using index matching of the representations of the 4D ultrasound images acquired previously and also during therapy. The physical frame-of-reference of the MR images are referenced to the radiation therapy system frame-of-reference so that the position of the treatment volume relative to the radiation therapy beam is determined.

In one embodiment, a system comprises one or more patient transports to move a patient into a magnetic resonance (MR) system and to a radiation therapy (RT) system; an ultrasound transducer attached to a patient, the ultrasound transducer mobile, hands-free, and electronically steerable, the ultrasound transducer configured to acquire four-dimensional (4D) images. A plurality of targets within the 4D volumes at each instance in time, at time point, t, can be identified by fiducial markers. The system thus comprises a controller having a processor configured to acquire acquisitions of real-time three-dimensional (3D) MR images ($M(\vec{r}, t)$) over time to produce 4D MR images, and real-time 3D ultrasound images ($U(\vec{r}, t)$) over time to produce 4D ultrasound images, the acquisitions temporally synchronized to a designated time point; and to generate a series of real-time transformation functions to identify fiducial markers from one or more of the 4D ultrasound images, $U(\vec{r}, t)$, at each time point (t), wherein the fiducial markers represent a unique respiration or motion state, $R_1(t)$, and link the corresponding 4D MR images, $M(\vec{r}, t)$, to the respective unique respiration or motion state.

In one aspect, the 4D images of the MR images link to a list of positions of the fiducial markers, the list of which represents different respiration or motion states as determined by the 4D ultrasound images. The system further comprises one or more secondary ultrasound images acquired during a radiation therapy (RT) procedure, wherein the respiration or motion states are matched to the 4D MR images during the RT procedure to determine a real-time designated respiration or motion state in the secondary ultrasound images. The system comprises a list of positions is represented by the equation: $R_1(t): U(\vec{r}, t) \to (\vec{r}, t)$, wherein $R_1(t)$ represents a collection of the positions of fiducial markers identified in the 4D ultrasound images at time, t, corresponding to a respective 4D MR image.

In embodiments of the system, the collection is a set of unique identifiers associated with different respiration or motion states as determined by the positions of the fiducial markers. In one aspect, the fiducial markers include one or more anatomical markers. In another aspect, the 4D MR images and the 4D ultrasound images are acquired asynchronously.

Embodiments further encompass a method for tracking a target during radiation therapy comprising the steps of: acquiring magnetic resonance (MR) images over time during a pre-treatment phase to account for respiratory motion or patient movement; acquiring, using an ultrasound device coupled to a patient, real-time three-dimensional (3D) ultrasound images over time to produce four-dimensional (4D) ultrasound images during a treatment phase for radiation therapy; temporally synchronizing the MR images and the 4D ultrasound images to an imaging time point; and generating a series of real-time transformation functions to identify one or more fiducial markers from one or more of the 4D ultrasound images at each time point, t, wherein the fiducial markers represent a respiratory or motion state, $R_1(t)$, and link one or more corresponding MR images, $M(\vec{r}, t)$, to the respiratory or motion state at the imaging time point. The MR images link to a list of positions of the fiducial markers in the 4D ultrasound images, the list of which represents different respiratory or motion states in the 4D ultrasound images. A step of acquiring secondary ultrasound images during an interval of the radiation therapy can determine a procedural motion state.

In one embodiment, the procedural motion state is converted to a set of numbers such that matching the set of numbers to the one or more fiducial markers selects out the MR image in real-time and determines the respiratory or motion states. The MR images are referenced to a radiation therapy system frame-of-reference to determine a position of a treatment volume relative to a radiation therapy beam. The real-time 4D ultrasound image identifies and labels each of the imaging time points and associates the imaging time point with the respiratory state or a selected motion state, and in view of corresponding soft tissue and tumor delineation in at least one of the MR images. In one aspect, the MR images and the real-time 4D ultrasound images are linked to related time points via image reconstruction methods.

Embodiments also include an integrated radiation therapy (RT) system comprising: one or more patient transports to move a patient into a magnetic resonance (MR) system and to a radiation therapy (RT) system; an ultrasound transducer attached to a patient, the ultrasound transducer mobile and electronically steerable; a controller having a processor configured to: acquire one or more real-time MR acquisitions and one or more real-time ultrasound acquisitions; temporally synchronize the one or more real-time MR acquisitions and the one or more real-time ultrasound acquisitions to a designated time point to provide one or more 4D MR images and one or more 4D ultrasound images, respectively; and generate a series of real-time transformation functions to identify fiducial markers from the one or more 4D ultrasound images, $U(\vec{r}, t)$, at each time point (t), wherein the fiducial markers represent a specific respiration or motion state, $R_1(t)$, and link one or more of the 4D MR images, $M(\vec{r}, t)$, to the specific respiration or motion state.

Aspects of the invention further comprise an acquisition of secondary ultrasound images obtained during a radiation therapy procedure, wherein the fiducial markers synchronize with the 4D MR images to determine a real-time respiration or motion state. The real-time MR acquisitions or the real-time ultrasound images can be a series of two-dimensional (2D) images acquired over time to obtain a 4D volume, or three-dimensional (3D) images acquired over time, to create the 4D MR images or the 4D ultrasound images, respectively. In one embodiment, the respiration or motion states in the 4D ultrasound images determines an MR-matched respiration or motion state by using index matching.

Embodiments of the invention, thus described, can be varied and reconfigured as desired to determine respiratory or other motion states, patient movement, environmental motion, or otherwise. Moreover, fusing the MR and ultrasound images assist in defining a unique respiratory state, the unique identifier of the respiration state derived from the procedural ultrasound images. Details are provided as follows.

DETAILED DESCRIPTION

The following detailed description of certain embodiments will be better understood when read in conjunction with the appended drawings. As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Although the various embodiments may be described herein within a particular operating environment, for example a particular imaging system, such as a particular magnetic resonance (MR) or ultrasound system, it should be appreciated that one or more embodiments are equally applicable for use with other configurations and systems.

Various embodiments provide systems and methods for using MR and ultrasound for tracking, such as real-time tracking (e.g., tracking while performing radiation therapy) of anatomical targets and correction of a radiation therapy treatment volume for respiration. In particular, various embodiments use the real-time imaging of ultrasound to identify and label each imaging time point and associate the designated time point with a respiratory state or selected motion state, with the soft tissue and tumor delineation of MR imaging. The ultrasound images and the MR images are linked to the same points in time via image reconstruction methods of interpolation or down-sampling such that MR images, $M(\vec{r}, t)$, at the same time point, t, as the corresponding ultrasound images, $U(\vec{r}, t)$, represent images acquired at a given respiration or motion state at time t. At least one technical effect of various embodiments is reduced likelihood of radiation exposure to healthy tissue. By practicing various embodiments, a low-cost, easy-to-use system for tracking anatomical targets to reduce the likelihood of exposure to healthy tissue, including critical organs, during radiation therapy (e.g., tumor radiation therapy) may be provided.

Figure 1:
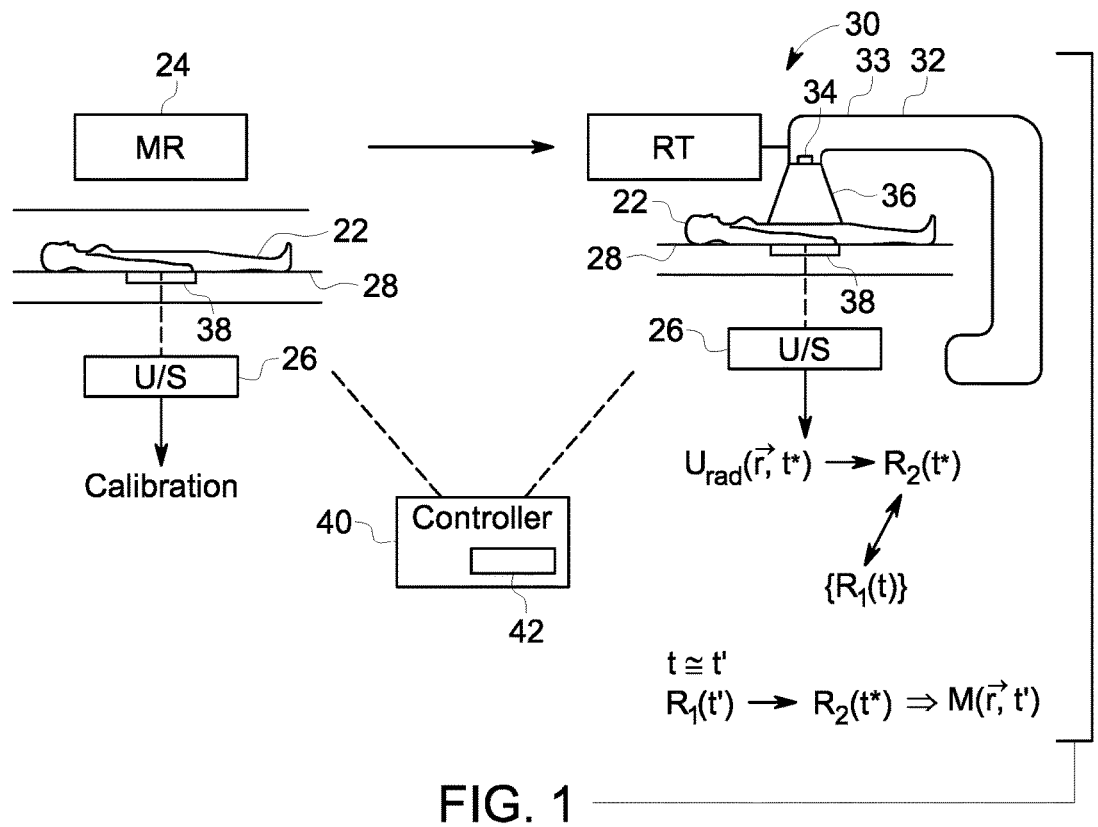
FIG. 1 is a diagram illustrating an anatomical tracking system in accordance with various embodiments.

In one embodiment, as illustrated in the system 20 shown in FIG. 1, a patient 22 undergoing radiation therapy, first undergoes a combined MR and ultrasound study that generates four-dimensional (4D) (three-dimensional space and time) MR and ultrasound images, which is referred to herein as the pre-treatment phase. The 4D MR images, represented by $U(\vec{r}, t)$, are acquired such that the image also may be used for radiation treatment planning. In particular, an MR system 24 in combination with an ultrasound system 26 are used to acquire MR images, represented by $M(\vec{r}, t)$, and ultrasound images of the patient 22, prior to radiation therapy treatment delivery. It should be noted that the positioning and relative location of the MR system 24 and the ultrasound 26 are shown merely for ease of illustration and simplicity, and the various components may be arranged different and may be combined or coupled differently in some embodiments.

The patient 22 is supported in a patient transport 28, such as a moving table or stretcher. In operation, after acquiring MR and ultrasound data, which may be used for calibration and correction of radiation therapy as described in more detail herein, the patient transport 28 is configured to move the patient 22 to a radiation therapy (RT) system 30 that in various embodiments includes a linear accelerator 33 (LINAC) for performing radiation therapy. In one embodiment, the patient transport 28, as shown, reduces and minimizes the variation of the patient's body habitus in moving between the MR scanner and the radiation therapy device (e.g., the LINAC). In practice, the pre-treatment acquisition in the MR system 24 could occur on a different day from the treatment phase on a radiation therapy (RT) system 30. In such a case, the patient transport used for the MR system 24 and the radiation therapy (RT) system may differ while sharing similar characteristics to minimize variations in organ displacement between systems. An example of such is a flat table-top. Variations are contemplated, such as a conformal patient bed that constrains the body habitus to the same form in both the MR scanner and radiation therapy device. In FIG. 1, the RT system 30 may include a gantry 32 that moves or controls a radiation source 34, which generates an x-ray beam towards a region of interest of the patient 22 (e.g., a region within the patient that includes a tumor). It should be noted that any suitable linear accelerator, such as one for external-beam radiation therapy may be used. In addition, it should also be noted that various embodiments including the methods described herein for image-guided radiation therapy are also applicable to therapy modes where energy beams other than x-ray are used. For example, various embodiments may be implemented in with particle (such as electron and proton beams) and/or heavy ion beam therapies.

In various embodiments, an ultrasound system 26, or a portion of the ultrasound system 26, is coupled or integrated into the patient transport 28, such as within or under a patient table. In some embodiments, the ultrasound system 26 is configured to allow operation in an MR and radiation environment, such that the ultrasound system 26 is shielded, for example, so as to not be affected by or to affect the operation of the MR or radiation systems. In one embodiment, an integrated ultrasound scanner or probe, which in one embodiment is a transducer array 38, is integrated or coupled with the patient transport 28. The transducer array 38 may have one or more different geometries as described in more detail herein and in various embodiments is configured to acquire ultrasound data of the patient 22 to generate 4D images, namely 3D images over time (i.e., 4D) that are used for radiation treatment planning for the radiation treatment system 30. In one embodiment, an integrated ultrasound transducer array 38 is electronically steerable to generate 4D images and can be secured to the patient via straps or suitable wraps.

More particularly, in various embodiments the patient transport 28 is a MR and radiation therapy compatible table. For example, in one embodiment, the patient transport 28 has the properties that the table-top and support structure forming the patient transport 28 are compatible with high magnetic fields (e.g., MR-compatible), in addition to being radio-translucent. The latter property allows photon beams to pass through the patient transport 28 without significant attenuation and scatter, which allows for accurate treatment planning and also reduces the radiation exposure to the patient 22 from scattering of the photon beam. It should be noted that in some embodiments (where additional radiation attenuation is desired) additional attenuation of the table structures may be accounted for in the treatment planning process, similar to attenuation correction in the reconstruction of positron emission tomography (PET) images. In one aspect, the patient transport used for the MR system 24 and the radiation therapy (RT) system are different but shares similar characteristics to minimize variations in organ displacement between systems; an example of such is a flat table-top. In such a case, the pre-treatment and radiation therapy phase can occur at different times so that the patient need not be transported between systems on the same patient transport, and can be repositioned on different transports.

The ultrasound transducer array 38 is also capable of operation in an MR environment as well as a high radiation environment. The transducer array 38 in some embodiments is a two-dimensional array capable of generating 4D images that allows real-time 3D images (i.e., 4D) to be generated electronically. In some embodiments, the transducer array 38 is configured to be less sensitive to high-energy photons (e.g., between 1-8 MeV) and can operate in an MR environment. In some embodiments, the transducer array 38 may be a one-dimensional array.

In various embodiments, a controller 40 that includes a processor 42 is provided. The controller 40 is configured to control the operation of the various components described herein, such as to perform real-time tracking and correction of a radiation treatment volume for respiration. A general description of the operations and configurations of the controller 40 will first be described followed by a more detailed description. In various embodiments, the controller 40 is configured to acquire and temporally synchronize the simultaneous acquisition of real-time 3D MR images ($M(\vec{r}, t)$) over time, as well as real-time 3D ultrasound images ($U(\vec{r}, t)$) over time (4D images), to the same or similar time points. The 4D ultrasound ($U(\vec{r}, t)$) and 4D MR images ($M(\vec{r}, t)$) synchronized to the same time points, t, represent the different respiratory or motion states specific at each time point, t. The controller 40 is also configured to generate a series of real-time transformation functions to identify fiducial markers from the ultrasound image, $U(\vec{r}, t)$, at each time point, t. The fiducial marker positions then represent a unique respiration or motion state, $R_1(t)$, and link the corresponding MR images, $M(\vec{r}, t)$, to the same respiration or motion state by virtue that the MR images are synchronized to the same time point, t. In particular, this setup, pre-treatment, calibration or training step to first identify the appropriate anatomical markers in the ultrasound image can be used as fiducials, and then used to generate a list of points that corresponds to the ultrasound image at time, t. Because the ultrasound and MR images are synchronized in time, the corresponding MR image at time, t, links to a list of marker positions that represent different respiration or motion states that are previously determined from the ultrasound image. This list of system components can be represented by:

$$R_1(t):U(\vec{r},t) \rightarrow M(\vec{r},t) \qquad \text{Eq. 1}$$

where $R_1(t)$ represents the collection of the position of anatomical markers identified in the ultrasound images at time, t corresponding to the MR image, and the collection is a set of unique identifiers (e.g., a set of numbers or indices) for different respiration or motion states. Each respiration or motion state may be represented by a plurality of unique identifiers, with each identifier determined from the position of one or more anatomical (fiducial) markers. Hence, for each respiration or motion state, $R_1(t)$, as determined from the ultrasound images, $U(\vec{r}, t)$, the corresponding MR images, $M(\vec{r}, t)$, that depict that respiration or motion state can be easily identified as $U(\vec{r}, t)$ and $M(\vec{r}, t)$, and are temporally linked. Note that no image spatial registration between ultrasound and MR images is needed to determine the MR images $M(\vec{r}, t)$ that correspond to a specific respiration or motion state, $R_1(t)$. To determine the MR images corresponding to a specific respiration or motion state, $R_1(t)$, the MR image set, $M(\vec{r}, t)$, is thus indexed to a specific time point, t.

The unique identifiers, $R_1(t)$, that represent the respiration or motion state is determined from the positions of one or more anatomical markers (i.e., fiducial markers). The multi-dimensional nature of the anatomical markers used to determine the unique identifiers, $R_1(t)$, can be any suitable method or algorithm that either matches or reduces positional variation to an index (e.g., numbers) or a set of indices (e.g., a set of numbers) that are unique to the position of the anatomical markers. It is assumed that each respiratory state or motion state is associated with a set of unique identifiers. In this manner, images acquired at a previous time that correspond to the respiratory state or motion state at some present time can be displayed and represent the current respiration or motion state.

If the MR and ultrasound images are acquired asynchronously, $R_1(t)$ in Equation 1 can still be determined, but a prior step of temporally synchronizing ($U(\vec{r}, t)$) and ($M(\vec{r}, t^*)$) is performed, where t and t* represent the ultrasound and MR images acquired at different times. The MR ($M(\vec{r}, t^*)$) and ultrasound ($U(\vec{r}, t)$) images can be temporally synchronized using temporal interpolation or down-sampling, individually or in combination, to linked image sets in Equation 1. It should be noted that the ultrasound images may also be acquired outside of the MR scanner if a prior step of fusing the asynchronously acquired MR and ultrasound images is performed. However, this adds complexity and uncertainty to the process as there needs to be high confidence and minimal error in the image fusion process, which can affect the time-varying spatial maps of the anatomical targets.

The controller 40 is also configured to control radiation treatment planning for each of the real-time MR images to deliver the prescribed dose to the target tumor. This is represented by:

$$M(\vec{r},t) \rightarrow PTV(t,\emptyset) \qquad \text{Eq. 2}$$

where Ø represents the angle of the gantry 32 (shown in FIG. 1) to deliver the prescribed dose to the target tumor volume accounting for the geometry and location of the tumor. It should be noted that there may be a series of angles, Ø, depending on the treatment plan and target dose to the tumor. It also should be noted that this control step may be performed in real-time if the computational capabilities are available. It also should be noted that in this embodiment, the PTV may vary in time as the position of the CTV, CTV ($\vec{r}$, t) changes with patient respiration or motion. In which case, the MR images, $M(\vec{r}, t)$, that are representative of the respiratory state or motion state, $R_1(t)$, are used to determine the PTV or if the CTV is within the treatment beam. Note that the objective of ensuring that MR image guidance is used to better control radiation therapy delivery to the tumor target or CTV is facilitated without utilizing the step of image fusion between MR and ultrasound images.

In various embodiments, the ultrasound transducer array 38 (shown in FIG. 1) acquires images in real-time and continuously while the photon beam therapy is occurring simultaneously. These images can be represented by ($U_{rad}$ ($\vec{r}$, t)). In various embodiments, the positions of the anatomical markers or fiducials, $R_2(t^*)$ are identified from ($U_{rad}(\vec{r}, t^*)$). In particular, by matching $R_2(t^*)$ with $R_1(t^*)$, the corresponding MR image, M($\vec{r}$, t), that was previously acquired can be displayed in real-time. In this manner, the MR images that represent the respiration or motion state given by $R_2(t^*)$, can be display in a rapid manner by simple matching of $R_2(t^*)$ with the pre-acquired respiration or motion states, $R_1(t^*)$, without utilizing physical image registration of ultrasound-to-ultrasound images or ultrasound-to-MR images. This is because the unique identifier of the respiration or motion state indicated by $R_2(t^*)$ is directly compared to the set of unique identifiers of respiration or motion state $R_1(t)$, as acquired during the pre-treatment phase to determine the MR images, M($\vec{r}$, t), that most closely resembles the respiration or motion state at time t* during the radiation (or photon beam) therapy phase. By matching the respiration or motion state at time t* with that of the pre-acquired, pre-treatment MR images, the tumor volume, critical organs, and other anatomical structures are identified and accessible without concurrent real-time MR scanning. In one aspect, the ultrasound images in both the pre-treatment acquisition and during radiation therapy are used for the determination of the respiration and motion state. In some embodiments, the ultrasound images may provide images of the tumor target or treatment volume. However, due to the poor soft tissue contrast of ultrasound images compared to MR images, the MR images are preferred to provide the imaging guidance during radiation therapy to identify the tumor target or treatment volume. Either may be utilized, however, as desired.

In various embodiments, the position of the CTV, CTV ($\vec{r}$, t) is indirectly determined from $R_2(t^*)$ as described above. For a static PTV, if CTV ($\vec{r}$, t) departs significantly from the static PTV, a control signal is sent to the linear actuator 33 (shown in FIG. 1) to modulate the photon therapy beam off. Once the CTV ($\vec{r}$, t) returns to the PTV location or volume, the photon therapy beam is modulated on. This control provides a therapy beam such that the radiation dose is delivered preferentially to the CTV rather than to healthy tissue or critical organs. In general, the control also tracks the amount of time the photon therapy beam is on for that specific treatment geometry angle, Ø, to provide adequate dose delivery to the tumor target, which is illustrated in FIG. 2.

Figure 2:
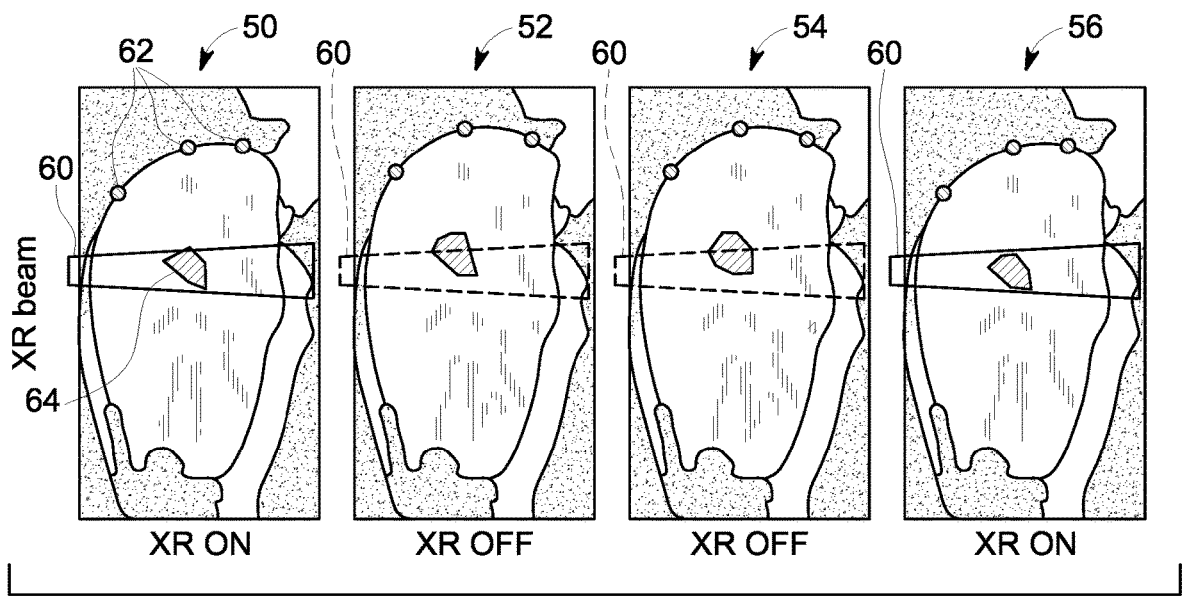
FIG. 2 are images illustrating modulation of a therapy beam in accordance with various embodiments.

For example, FIG. 2 shows the modulation of a photon therapy beam (XR) 60 for a fixed PTV on MR images 50, 52, 54 and 56 at different points in time. In the illustrated example, XR is on for images 50 and 56 and off for images 52 and 54. The circles 62 in each of the images 50, 52, 54 and 56 indicate representative anatomical markers corresponding to the MR images at time t, M($\vec{r}$, t), while the regions 64 represent the CTV, which as can be seen, varies in shape and size over time. By relating M($\vec{r}$, t) with $R_2(t^*)$ that was determined from the real-time ultrasound images $U_{rad}(\vec{r}, t^*)$, a determination can be made as to whether the CTV is within the static PTV. Accordingly, as shown in FIG. 2, during a time period (corresponding to the images 50 and 56), when the CTV is within the static PTV, XR is turned on and during a time period (corresponding to the images 52 and 54), when the CTV is not within the static PTV, for example, a least a portion (e.g., any portion or a define amount) of the CTV is not within the static PTV, the XR is turned off. In some embodiments, XR is turned or modulated off only when there are significant deviations of the CTV from the PTV.

To perform the above-mentioned function of determining if the CTV is within the static PTV, the physical coordinates of the MR images are determined and synchronized with the physical coordinates of the radiation therapy system prior to commencing therapy through procedures that are currently used in the radiation therapy protocol. For example, the usual practice is to use an X-ray image to match treatment planning image coordinate system with the physical coordinate system of the radiation therapy system.

In another embodiment, the PTV (t, Ø) is indirectly determined, in real-time from the measured $R_2(t^*)$ points by the matching process described above. This is the PTV that corresponds to the positional variation of the CTV ($\vec{r}$, t). In various embodiments, the commands to the linear actuator 33 are transmitted (e.g., by the controller through a wired or wireless link) to adjust a collimator (e.g., a multi-leaf collimator (MLC) of the RT system 30) to generate a dynamic PTV (t, Ø). This process provides for the correct radiation dose to be delivered to the CTV and reduces the likelihood or avoids additional radiation damage to healthy tissue. Additionally, the PTV may be positioned closer to the CTV, such as closer than in conventional systems. Additionally, this process is expedient as the photon therapy beam is always on, also reducing or minimizing the overall treatment time per radiation dose partition. This set up also allows the operator or clinician to monitor the changes in the PTV in relation to the changing position of the tumor target in real-time.

Figure 3:
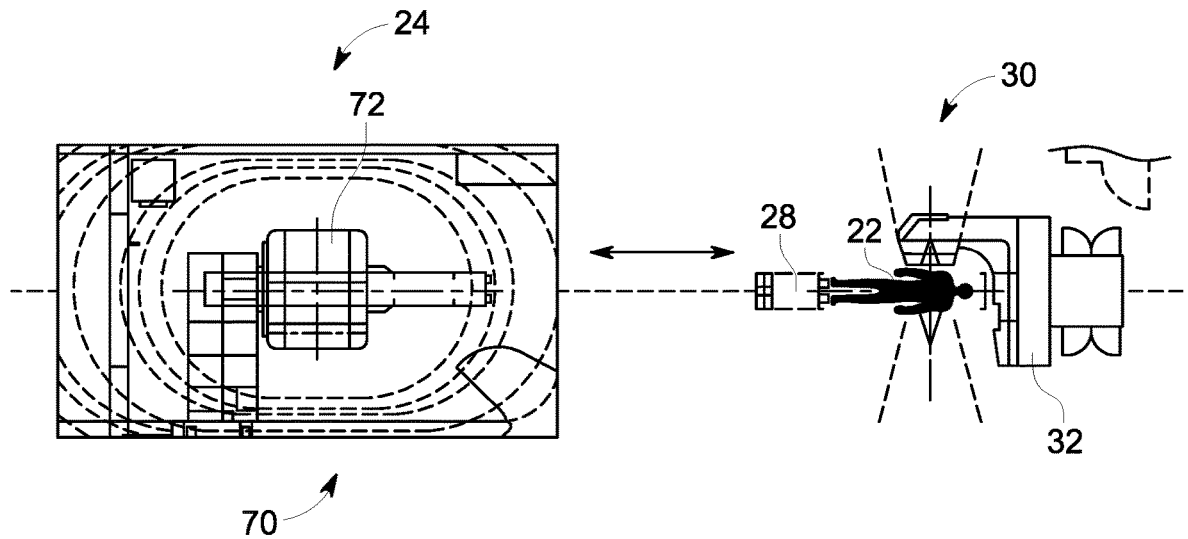
FIG. 3 is a diagram illustrating a device configuration in accordance with an embodiment.

With respect to workflow, the patient 22 will first be imaged by the MR system 24 (which includes an MR scanner 72 in various embodiments as shown in FIG. 3) on the radiation-therapy compatible patient transport 28 with the ultrasound scanner 38. In operation, real-time MR images are acquired simultaneously with the real-time ultrasound images. The patient 22 is then moved to the RT system 30 for therapy. It should be noted that treatment planning can occur at any time after the MR images are acquired. As such, the patient transport 28 used in the MR system 24 may be different than that utilized in the therapy system 30 but shares some physical characteristics, such as having a flat table-top. One embodiment of a configuration for a room set-up 70 and patient transition is shown in FIG. 3, wherein the patient transition is illustrated by the arrow. As can be seen, the patient 22 is maintained on the patient transport 28 and in this embodiment movement of the patient transport 28 is generally linearly from the MR scanner 72 to the RT system 30. However, it should be appreciated that the patient transport 28 may be moved transversely, such as to an angle with respect to the arrow, for example, based on the positioning of the RT system 30, which may not be able to be in line with the scanner 72 in some embodiments as a result of the room dimensions or size. It should also be noted that various embodiments may be implemented in other therapy protocols. For example, a therapy protocol where the patient is moved more than once between the MR scanner and the radiation therapy device to reposition the PTV or to assess tissue changes after radiation therapy to better determine treatment efficacy.

The room set-up 70 is one example of a configuration that provides image guided radiation therapy. It should be noted that the patient 22 in some embodiments may be moved between different rooms. In the illustrated embodiment, the MR scan is first performed to identify the tumor(s) margins and determine the PTV. The patient is then transported to the RT system 30 using the same patient transport 28 having the transducer array 38 or other ultrasound scanner or probe that is capable of 4D imaging is some embodiments. Thus, soft tissue contrast images acquired using the transducer array 38 in real-time may be used to guide the definition of radiation therapy treatment volumes, such as the photon beam definition (e.g., photon beam shape or profile).

As should be appreciated, in accordance with various embodiments, both the MR system 24 and the RT system 30 are not modified except that that the patient transport 28 includes or has integrated therewith ultrasound capability.

As should be appreciated, in accordance with various embodiments, the patient transport 28 for the MR system 24 and the RT system 30 may not be necessarily identical but need to share the same characteristics, such as a flat tabletop, or some other feature that allows the internal organs to maintain the same relative positions between systems. Such additional characteristic could also be a conformal, custom body mold, in one embodiment.

Various embodiments use real-time ultrasound to indirectly obtain high spatial resolution images of the tumor(s) without incurring additional radiation risk or cost. In particular, the higher resolution MR images acquired during the pre-treatment phase are correlated to the 4D ultrasound images acquired during the treatment phase. During the treatment phase, 4D ultrasound images are acquired and are then mapped into the pre-treatment 4D ultrasound images, through matching the unique identifiers between $R_2(t^*)$ during treatment, and the unique identifiers, $R_1(t)$, determined during the pre-treatment. There is a correlation between the pre-treatment 4D ultrasound images, $U(\vec{r}, t)$, and the higher resolution MR images, $M(\vec{r}, t)$, because both are synchronized in time. Hence, by mapping or matching the treatment 4D ultrasound images, $U_{rad}(\vec{r}, t^*)$, to the pre-treatment 4D ultrasound images, $U(\vec{r}, t)$, using the unique identifiers, $R_2(t^*)$ to $R_1(t)$, the treatment respiration or motion state at time t* can be indirectly correlated to higher resolution MR images that reflect the same spatial disposition of the critical organs and tissue in the treatment target area. Hence, the treatment real-time 4D ultrasound images indirectly "obtains" or "acquires" higher resolution MR images that reflect the same spatial position of the anatomy at a specific time point using a method of matching unique respiration or motion state identifiers rather than image registration, which is a much more rapid and time-efficient process.

It should be noted that in various embodiments, real-time refers to obtaining information or performing tracking while performing radiation therapy. In some embodiments, as described in more detail herein, a 4D ultrasound imaging platform may be used during the treatment planning (MR) phase to calibrate the range of motion of the RT system 30 over time and then use the same ultrasound imaging platform to provide real-time tracking and guidance during radiation therapy by the RT system 30. By having high definition images of the tumor in real-time (e.g., higher resolution than ultrasound images), the PTV can be modified dynamically and/or in real-time to adapt the treatment volume to track or map the tumor volume as the volume changes position or deforms during respiration.

Figure 4:
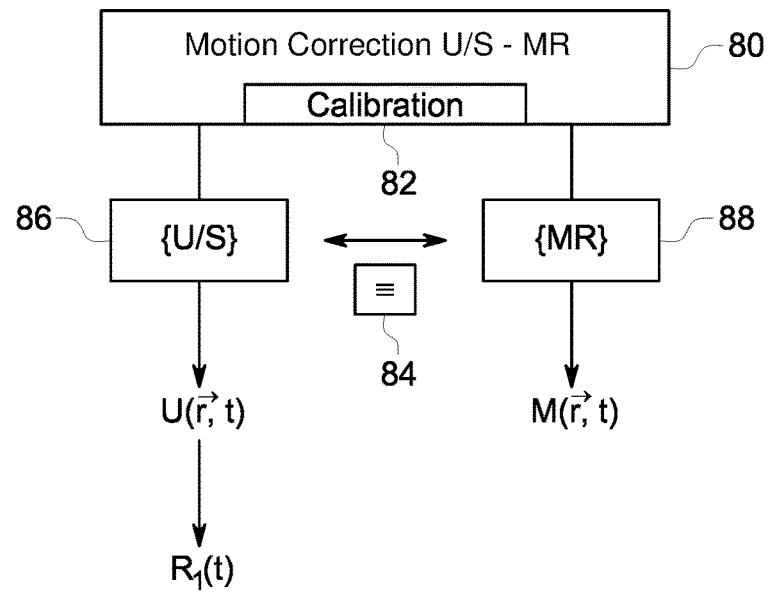
FIG. 4 is a block diagram illustrating a motion correction module in accordance with various embodiments.

In some embodiments, a motion correction module 80 as shown in FIG. 4 may be provided. The motion correction module 80 may be implemented in hardware, software or a combination thereof, and may be provided as part of or accessed by the controller 40 (shown in FIG. 1). The motion correction module also may include a calibration sub-module 82 to perform calibration operations as described herein.

Figure 5:
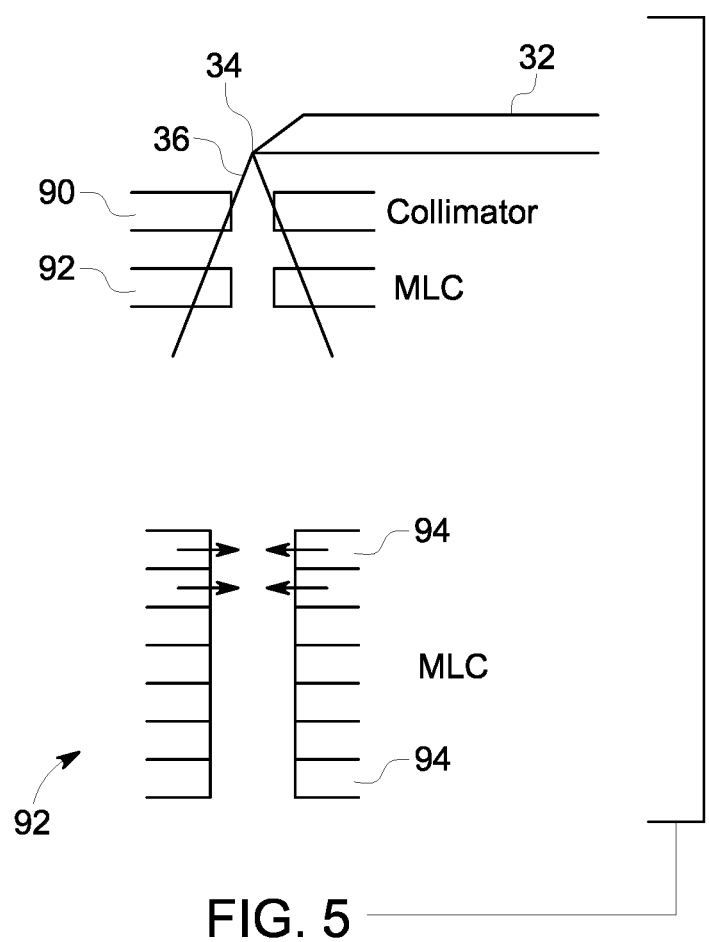
FIG. 5 is a diagram illustrating a collimator arrangement in accordance with one embodiment.

In operation, from the prior MR-ultrasound pre-treatment study (acquisition of MR and ultrasound images), transformation-relationship tables 84 are computed to correlate the ultrasound images 86 with the MR 4D images 88. Using these transformation tables 84, the ultrasound only real-time 4D images acquired during the radiation therapy procedure will produce accurate, corresponding high spatial resolution MR images. The transformation-relationship tables 84 are computed using the unique identifiers determined in $R_2(t^*)$ and $R_1(t)$, representing pre-treatment and treatment respiration or motion states. The MR and ultrasound images are linked as they are temporally synchronized to the same time points, t. These images can be used dynamically and/or in real-time to enable/disable the radiation beam if the CTV is deviates from the PTV. Additionally, various embodiments may also, in real-time, re-compute and modulate the PTV in response to changing location and/or shape of the CTV as a result of respiration. For example, as shown in FIG. 5, in some embodiments, the RT system 30 includes a collimator 90 positioned adjacent the radiation source 34 and a MLC 92 positioned adjacent the collimator 90. It should be noted that adjacent may refer to in physical contact or separated by a gap.

The MLC 92 includes movable segments 94 that be adjusted, as illustrated by the arrows to adjust the collimation of the beam 36. For example, the MLC 92 may be used to control the PTV shape for intensity modulated radiation therapy (IMRT). The MLC 92 can be reconfigured in some embodiments, for example, in as little as 120 ms. Hence, real-time control over the PTV may be provided to perform real-time radiation planning.

In accordance with various embodiments, during radiation treatment planning, the PTV size is reduced or made smaller and positioned closer to the CTV in order to reduce or avoid radiation damage to healthy tissue. The PTV accounts for changes in the target tumor from respiration and also accounts for differences in geometry. In various embodiments, maximum radiation dose is increased or maximized to the tumor volume (CTV) while reducing or minimizing radiation dose to healthy tissue and also to nearby critical organs. Various embodiments provide MR-like or MR images without constructing a combined MR-RT system.

Various embodiments use ultrasound to provide real-time images of anatomical landmarks and to map those landmarks to a corresponding MR image that has been pre-acquired. Accordingly, real-time MR images can be indirectly generated to provide real-time image guidance for control of the radiation therapy treatment volume.

Figure 6:
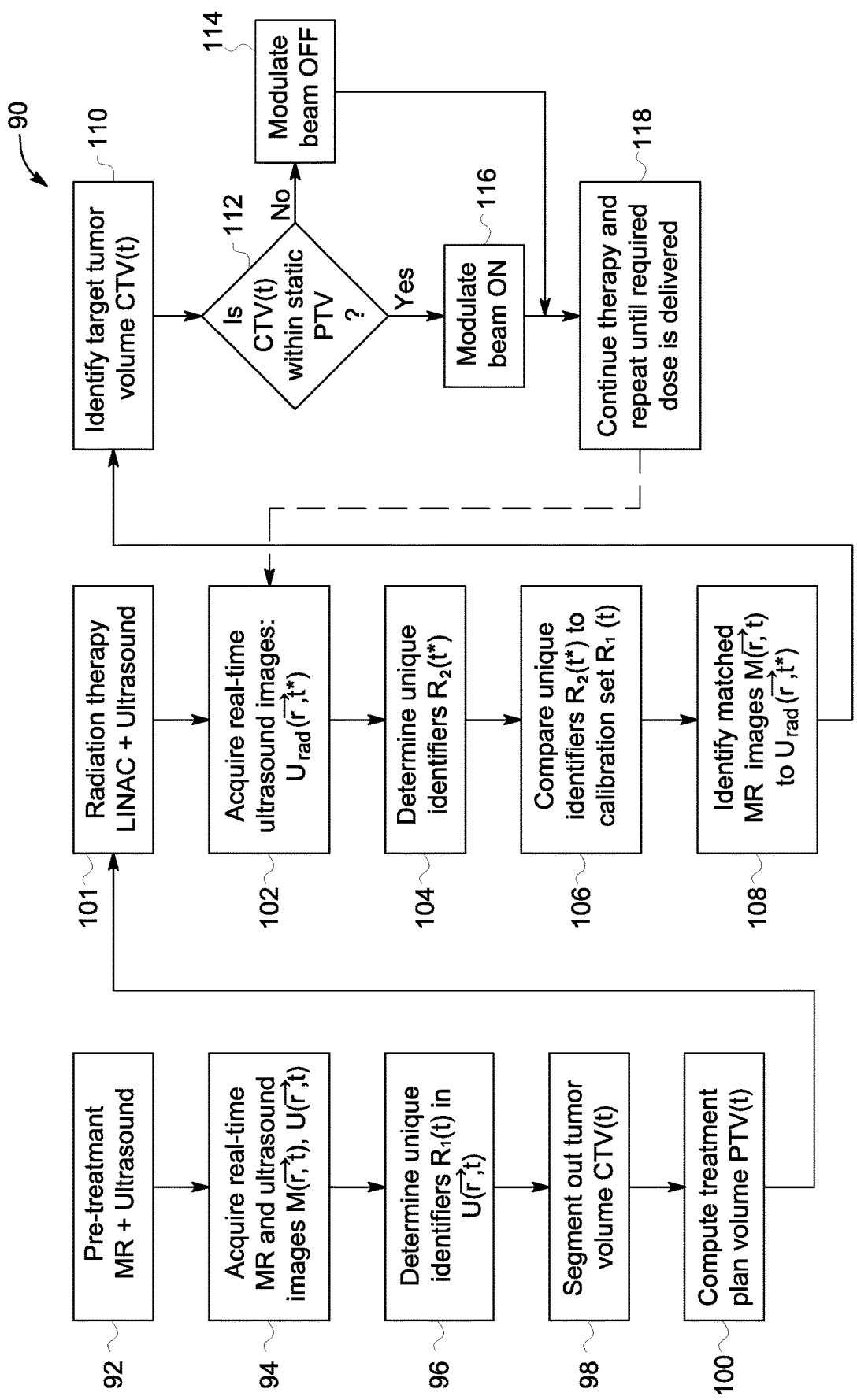
FIG. 6 is flowchart of a method in accordance with an embodiment.

In one embodiment, from the real-time ultrasound images acquired during radiation therapy, $U_{rad}(\vec{r}, t^*)$, the unique identifiers, $R_2(t^*)$ are determined from positions of anatomical markers. The unique identifiers are then compared and matched to the set of unique identifiers, $R_1(t)$, that were acquired in the pre-treatment phase of the therapy procedure as diagrammatically illustrated in FIG. 1. The corresponding MR images, $M(\vec{r}, t^*)$ that were previously acquired that correspond to the respiration or motion state at time $t^*$ are identified. That is, if unique identifiers $R_1(t)$ matches $R_2(t^*)$, then the pre-acquired MR images, $M(\vec{r}, t)$, with the time index, t, provides a high-spatial resolution image that most closely matches the physical respiration or motion state at that time, $t^*$, during the treatment phase. From this identification, the target clinical tumor volume, CTV (t) is determined in real-time. If a fixed planning treatment volume, PTV, is used, then if CTV(t)∈PTV is within δ, where δ is a tolerance factor, then the radiation therapy beam is modulated on. If not, the beam is modulated off. FIG. 6 is a flowchart 90 illustrating a method for real-time image guided radiation therapy for a fixed planning treatment volume CTV, wherein, if the identified target tumor volume(s), CTV(t) falls outside of the PTV, subject to the tolerance factor δ, the radiation beam is modulated off. The flowchart 90 will be described in more detail below.

Figure 7:
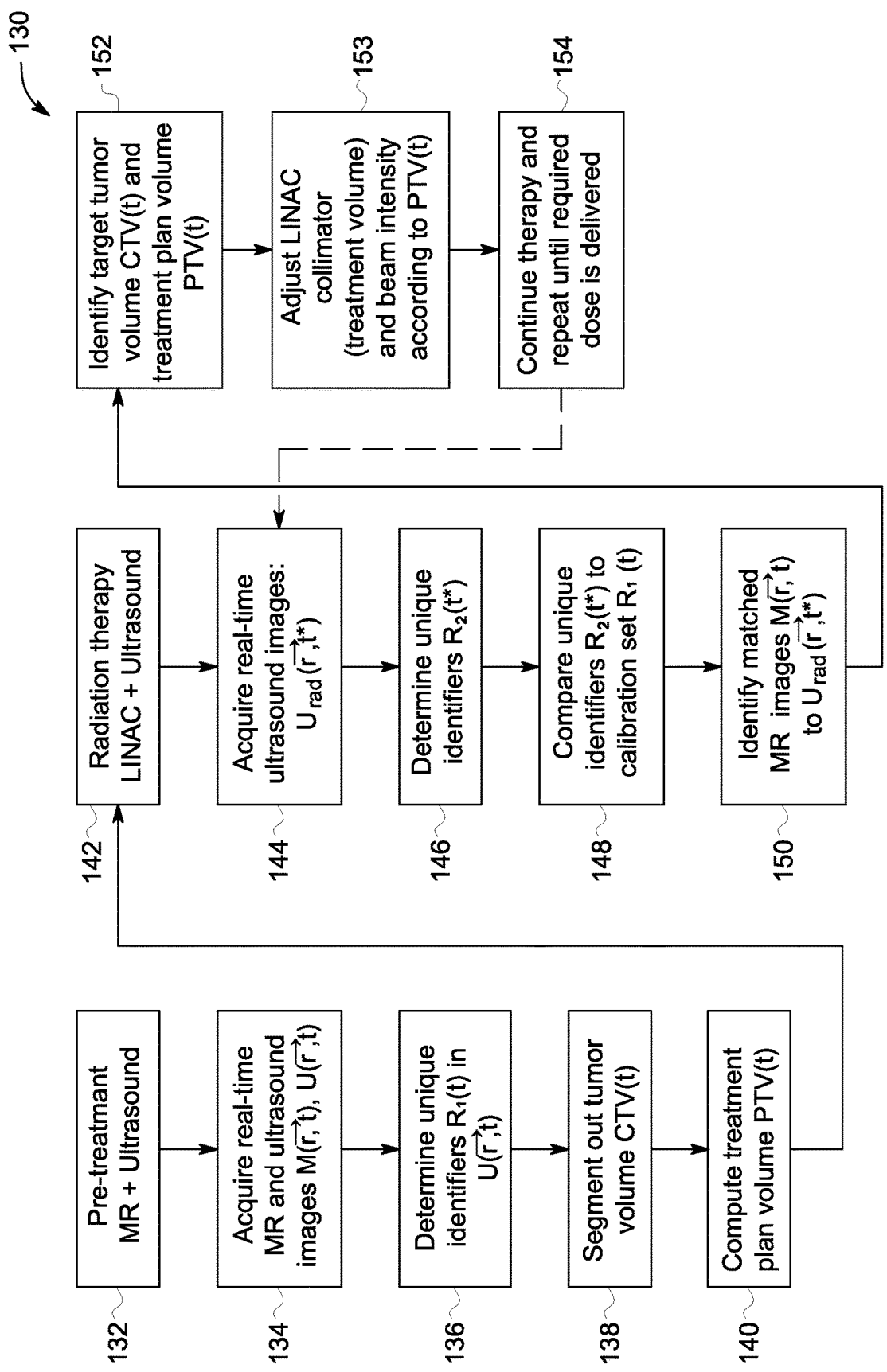
FIG. 7 is a flowchart of a method in accordance with another embodiment.

In another embodiment, from the real-time ultrasound images acquired during radiation therapy, $U_{rad}(\vec{r}, t^*)$, the unique identifiers, $R_2(t^*)$ are determined. These markers are then compared and matched to the set of unique identifiers, $R_1(t)$, that were acquired and determined in the pre-treatment phase of the therapy procedure. The corresponding previously acquired MR images, $M(\vec{r}, t)$, with the time index, t, that most closely matches the physical respiration or motion state at that time, $t^*$, during the treatment phase are identified in real-time. From this identification, the target clinical tumor volume, CTV(t), as well as the planning treatment volume, PTV(t) for this time point, $t^*$ is identified, in real-time. The MR images, $M(\vec{r}, t^*)$, with the tumor volume as an overlay can be displayed in real-time. As the corresponding planning treatment volume is also known for that time point, PTV ($t^*$), control signals may be sent to the RT system 30 to modulate the radiation therapy beam intensity (for that particular beam geometry, Ø, and also to control the MLC 92 (shown in FIG. 5) to adjust the radiation field to give the correct PTV for that given geometry during a radiation therapy session. For example, FIG. 7 illustrates a flowchart of a method 130 for real-time image guided radiation therapy in accordance with an embodiment that adapts the planning treatment volume, PTV(t), as a function of time in response to the changing position and shape of the target volume, CTV(t). In this embodiment, control signals may be sent to the RT system 30 to change the beam shape and modulate the intensity of the radiation for the given treatment geometry.

In particular, and with reference now to the method 90 shown in FIG. 6, at 92, pre-treatment MR+ultrasound is performed. For example, as described herein, real-time MR and ultrasound images of the patient may be acquired concurrently at 94 using the MR system 24 and ultrasound system 26. Thereafter, the unique identifiers are determined at 96 from the ultrasound images and the tumor volume is segmented out at 98 from the MR images. For example, any suitable segmentation process may be used to identify the tumor including using automated or semi-automated methods in the art. Using the segmented tumor volume, a treatment plan volume is computed at 100. At this point, the patient may be moved to the RT system 30. Note that at 96 and 98, the ultrasound and MR images, respectively, are linked by virtue of being synchronized in time.

Radiation therapy, which includes linear movement of the radiation source+ultrasound, may be performed at 101. This process includes acquiring real-time ultrasound images at 102 and determining the unique identifiers at 104 that represent or depict the respiration or motion state. Then at 106, the unique identifiers at 104 are compared to the unique identifiers from the calibration set, namely the anatomical markers identified at 96. Using this comparison, matched MR images may be identified at 108, such as based on images having the closest aligned marker positions or set of unique identifiers. The target tumor volume is then identified at 110 and a determination made at 112 as to whether the target tumor volume is within the static treatment plan volume. If the target tumor volume is not within the static treatment plan volume, then the radiation beam is modulated off at 114. If the target volume is within the static treatment plan volume, then the radiation beam is modulated on at 116. The radiation beam is repeatedly applied until the desired dose is delivered, which includes returning to step 102 after each beam application or periodically.

With reference now to the method 130 shown in FIG. 7, at 132, pre-treatment MR+ultrasound is performed. For example, as described herein, real-time MR and ultrasound images of the patient may be acquired concurrently at 134 using the MR system 24 and ultrasound system 26. Thereafter, unique identifiers are determined at 136 and the tumor volume is segmented out at 138. For example, any suitable segmentation process may be used to identify the tumor including using automated or semi-automated methods in the art. Using the segmented tumor volume, a treatment plan volume is computed at 140. At this point, the patient may be moved to the RT system 30.

Radiation therapy, which includes linear movement of the radiation source+ultrasound, may be performed at 142. This process includes acquiring real-time ultrasound images at 144 and determining unique identifiers at 146. Then, at 148, the unique identifiers at 146 are compared to the unique identifiers from the calibration (pre-treatment) set, namely the unique identifiers at 136. A match then correctly identifies the calibration (pre-treatment) images that most closely corresponds to the current respiration or motion state. Using this comparison, matched MR images may be identified and extracted at 150, such as based on images having the closest aligned marker positions or set of unique identifiers. The target tumor volume and treatment plan volume are then identified at 152 and the collimator of the RT system 30, for example, the MLC 92 is adjusted to adjust the treatment volume and/or the beam intensity 153 according to the treatment plan volume. The radiation beam is repeatedly applied until the desired dose is delivered 154, which includes returning to step 144 after each beam application or periodically.

Figure 8:
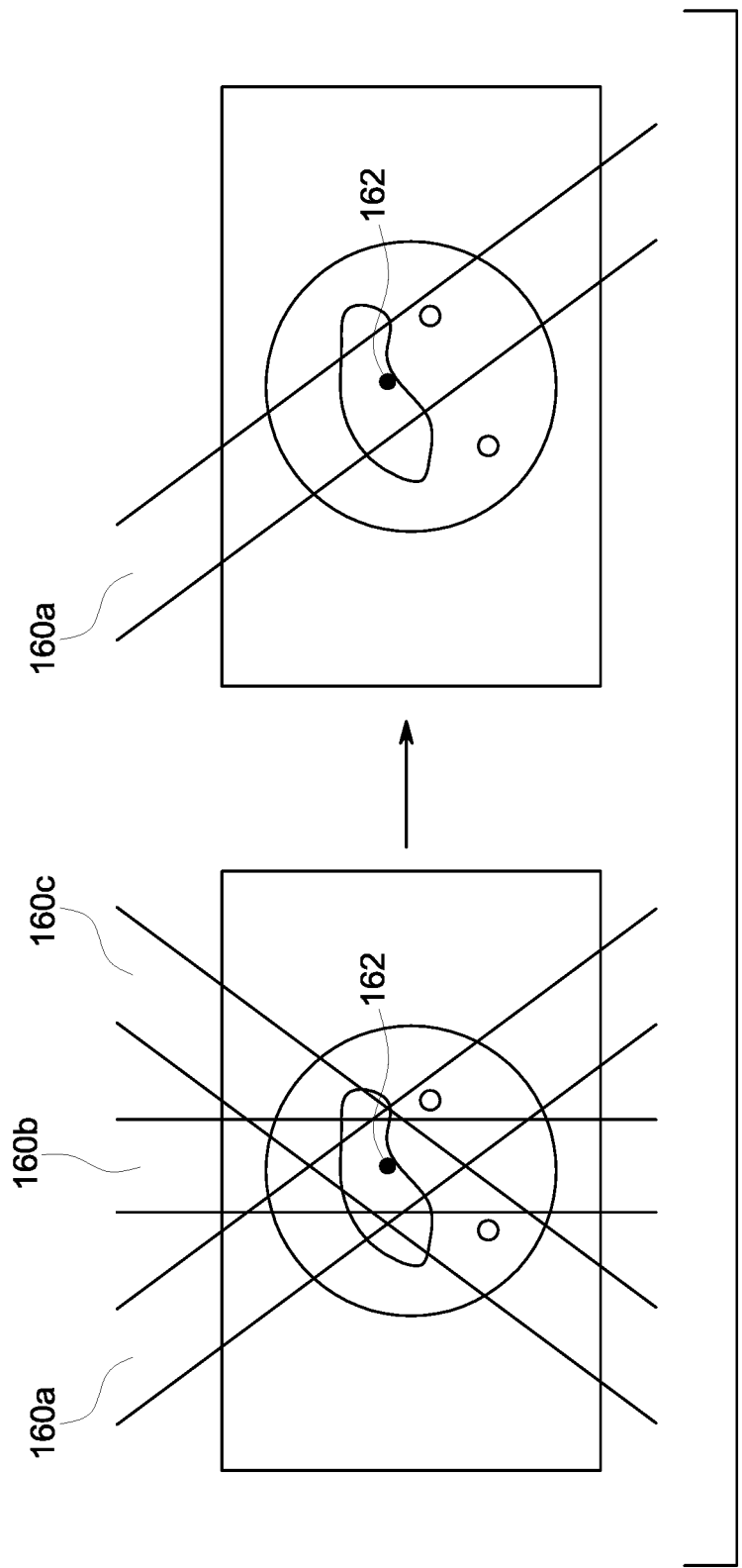
FIG. 8 is a diagram illustrating therapy modulation in accordance with an embodiment.

Thus, for example, as illustrated in FIG. 8, when the patient is not breathing, the beams 160*a*-*c* are applied to the tumor 162. However, when the patient breathes, in some embodiments the beams are modulated off or some of the beams are modulated off, which in FIG. 8 illustrates applying beam 160*a* and then waiting to apply beams 160*b* and 160*c* until the patient stops breathing (wherein the dashed lines represents movement of the patient due to breathing.

Thus, various embodiments provide a method for real-time tracking of the anatomy and anatomical targets in a system that includes an MR and high energy x-ray compatible table and patient transport capable of moving a patient into both an MR scanner and a LINAC and an MR and high energy x-ray compatible ultrasound transducer integrated into a patient transport capable of producing real-time 4D ultrasound images concurrently or simultaneously with either an MR real-time image acquisition or during radiation therapy from the LINAC. The system may also have separate patient transports that are unique to the MR and LINAC systems, respectively. The system also includes a platform that integrates image information from ultrasound and MR imaging systems and is able to control the photon beam definition (e.g., distribution) and intensity modulation in the LINAC. In some embodiments, concurrent or simultaneous acquisition of real-time 4D MR and ultrasound images are provided during a pre-treatment phase and the acquisition of the real-time 4D MR and ultrasound images are temporally synchronized such that there is a one-to-one temporal correspondence between the MR and ultrasound images. The MR images are denoted as $M(\vec{r}, t)$ and the ultrasound images are denoted as $U(\vec{r}, t)$, with the MR and ultrasound images representing the patient respiration or motion state at time, t. Aspects of the invention refer to motion state as representative of any motion of the patient, including, without limitation, autonomous nervous system functions that regulate internal organs such as the heart, stomach, intestines, and some musculatory functions, among others.

In some embodiments, anatomical or fiducial markers are identified in the ultrasound image as a function of time and the MR images as a function of time, wherein the ultrasound and MR anatomical markers in a calibration segment in the pre-treatment phase are correlated. Also, a mathematical relationship, $R_1(t)$, may be derived to allow mapping of the ultrasound images, $U(\vec{r}, t)$, to the corresponding MR images, $M(\vec{r}, t)$, wherein $R_1(t)$ may represent a collection of anatomical markers or fiducials converted into a unique identifier set in the ultrasound image, $U(\vec{r}, t)$ and the identification of $R_1(t)$ allows the indirect linkage to the corresponding MR image, $M(\vec{r}, t)$ through the ultrasound image, $U(\vec{r}, t)$, alone, as the ultrasound and MR images are temporally linked to the same time point, t.

Additionally, in the treatment phase when the patient is in the RT system 30, the integrated ultrasound transducer may produce real-time images $U_{rad}(\vec{r}, t^*)$, where $t^*$ is the time reference frame when the patient is undergoing therapy on the RT system 30. During the treatment phase, when the patient is in RT system 30, anatomical or fiducial marker positions in $U_{rad}(\vec{r}, t^*)$ may be determined and represented by a set of unique identifiers, $R_2(t^*)$. Also, in the treatment phase, the anatomical or fiducial marker positions are determined and represented by a set of unique identifiers, $R_2(t^*)$, that have been identified and may be compared to that in the calibration or pre-treatment phase, $R_1(t)$. During the treatment phase, it should be noted that the comparisons between $R_2(t^*)$ to $R_1(t)$ yield the correct identification of the MR image, $M(\vec{r}, t)$ that corresponds to the current respiration or motion state at time, $t^*$, using the real-time ultrasound image, $U_{rad}(\vec{r}, t^*)$. The corresponding, high spatial resolution and high contrast definition MR image, $M(\vec{r}, t)$ that represents the anatomy at time $t=t^*$ may be displayed and utilized in controlling the radiation therapy beam.

In the treatment phase, the target tumor volume that was previously segmented in the pre-treatment phase from the MR images, $M(\vec{r}, t)$ may be displayed in real-time from the correct identification of the MR image that corresponds to the current respiration or motion state at time, $t^*$, using the mapping, or matching of the set of unique identifiers, of $R_2(t^*)$ to $R_1(t)$. Also, in the treatment phase, where the treatment planning volume (PTV) is computed in real-time to conform, with adequate margins, to the clinical treatment volume of the identified tumor, control sequence commands may be communicated to the RT system 30 to control both the intensity and spatial distribution of the applied radiation treatment beam to the tumor volume.

In the treatment phase, where the treatment planning volume (PTV) was computed prior to the treatment phase and is unique in time, PTV(t) and corresponds to the prior MR images, $M(\vec{r}, t)$ and where the planning treatment volume, PTV (t), varies with the changes in the tumor volume that is reflected in $M(\vec{r}, t)$ and conforms with adequate margins, to the clinical treatment volume of the identified tumor, control sequence commands may be transmitted to the RT system 30 to control both the intensity and spatial distribution of the applied radiation treatment beam to the tumor volume.

Further, in the treatment phase, having a fixed treatment planning volume (PTV), as an alternative treatment embodiment, is to compare the position of the tumor volume in $M(\vec{r}, t)$ as indirectly determined from $U_{rad}(\vec{r}, t)$ (via the matching of unique identifiers, $R_2(t^*)$ to $R_1(t)$) to determine if the target tumor volume is within the volume of the fixed PTV and control sequence commands may be transmitted to the RT system 30 to modulate the applied radiation therapy beam on or off depending on if the target tumor volume is within or not completely within the fixed PTV (using a defined or pre-determined criteria), respectively.

Figure 9:
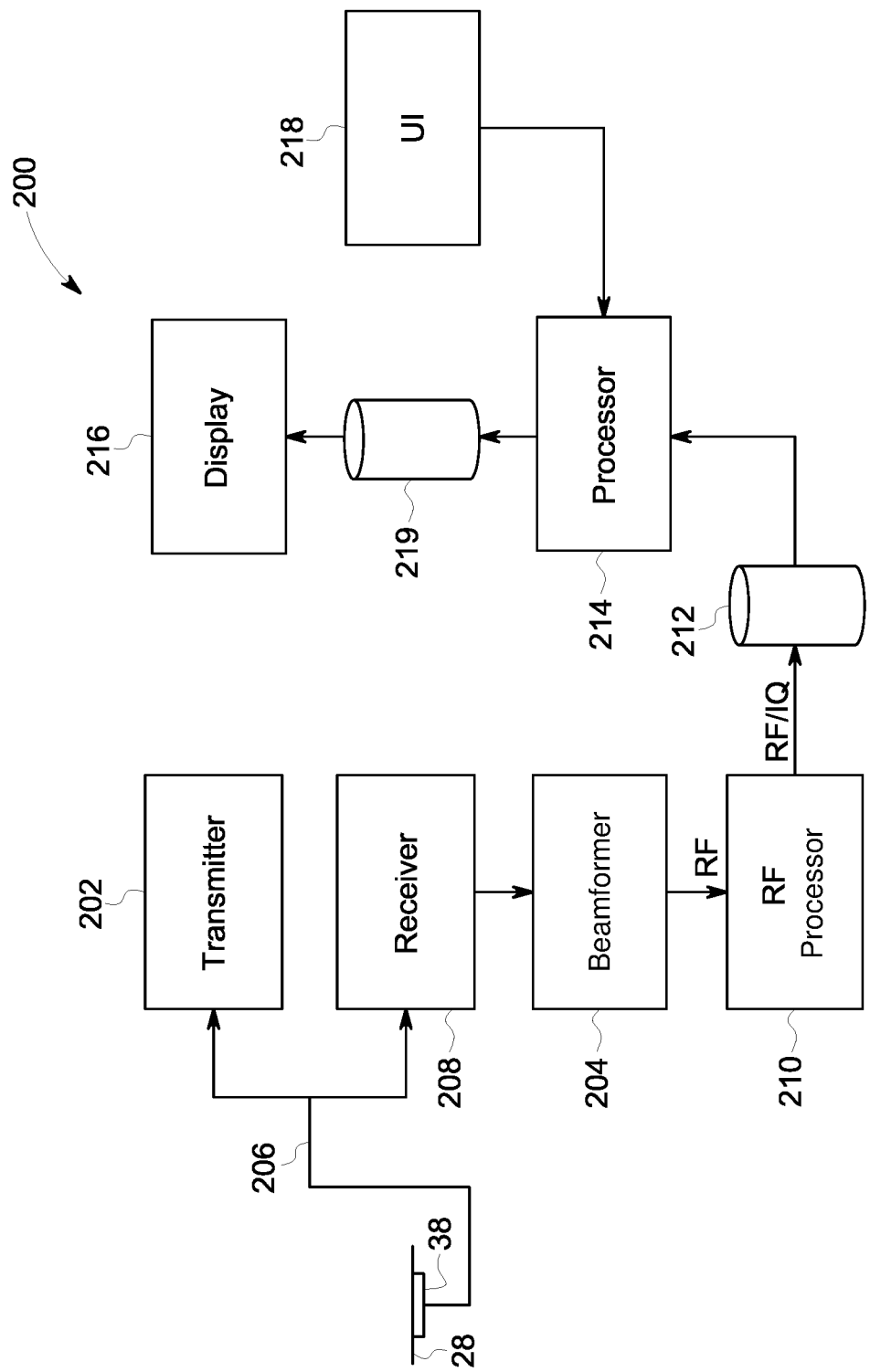
FIG. 9 is a block diagram of an ultrasound system in accordance with an embodiment.

It should be noted that the MR system 24, the ultrasound system 26, and the RT system 30 may be provided in different configurations. For example, FIG. 9 illustrates an embodiment of an ultrasound system 200 that may be used and, for example, be embodied as the ultrasound system 26.

The ultrasound system 200 is capable of electrical or mechanical steering of a soundbeam (such as in 3D space) and is configurable to acquire information (e.g., image slices) corresponding to a plurality of 2D or 3D representations or images of a region of interest (ROI) in a subject or patient, which may be defined or adjusted as described in more detail herein and acquired over time (4D). The ultrasound system 200 is also configurable to acquire 2D images in one or more planes of orientation.

Figure 10:
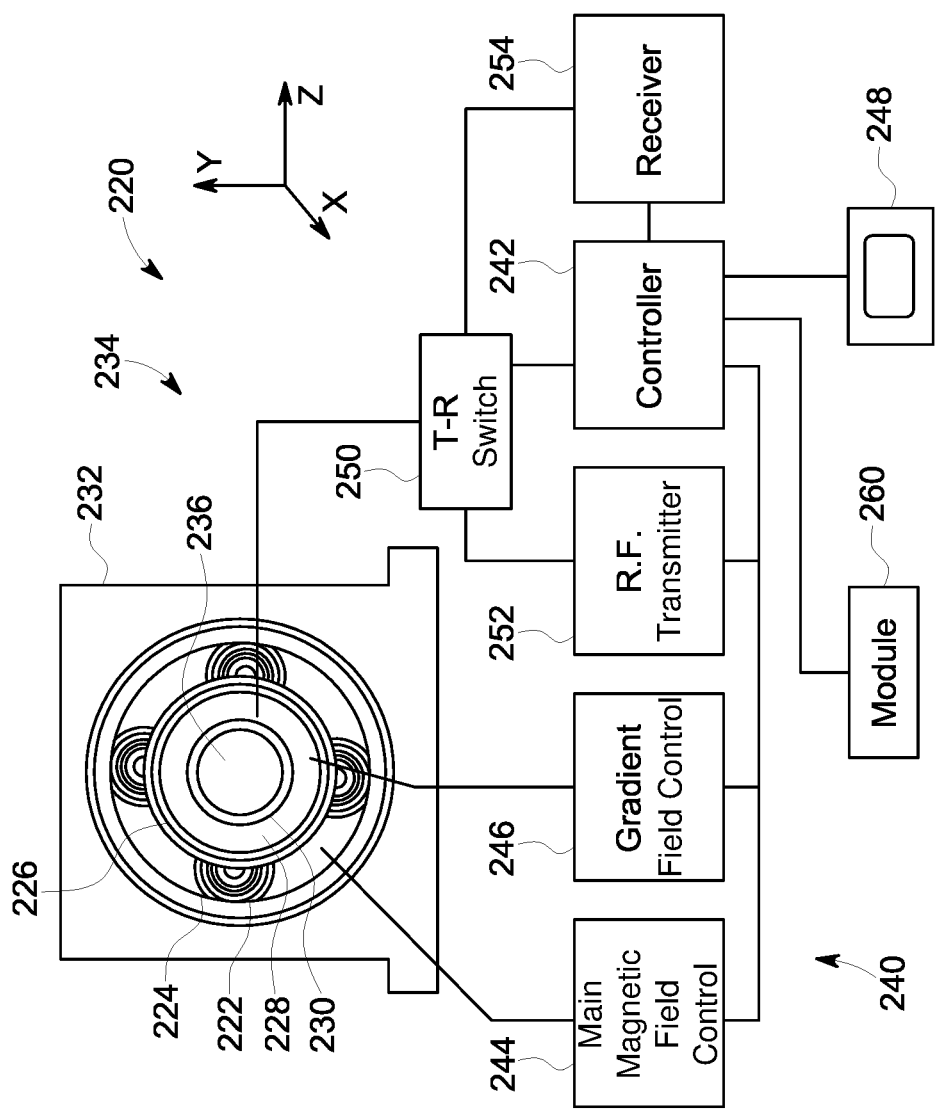
FIG. 10 is a block diagram of a magnetic resonance imaging (MRI) system in accordance with an embodiment.

The ultrasound system 200 includes a transmitter 202 that, under the guidance of a beamformer 204, drives an array of elements (e.g., piezoelectric elements), which may be embodied as the transducer array 38, to emit pulsed ultrasonic signals, i.e. sound waves, into a body. In some embodiments, a probe may be utilized as the ultrasound transducer. A variety of geometries may be used. As shown in FIG. 10, the transducer array 38 may be coupled to the transmitter 212 via the system cable 206 (which may include an interface). The sound waves are reflected from structures in the body to produce echoes that return to the elements of the transducer array 38. The echoes are received by a receiver 208. The received echoes are passed through the beamformer 2-4, which performs receive beamforming and outputs an RF signal. The RF signal then passes through an RF processor 210. Optionally, the RF processor 201 may include a complex demodulator (not shown) that demodulates the RF signal to form IQ data pairs representative of the echo signals. The RF or IQ signal data may then be routed directly to a buffer 212 for storage.

In the above-described embodiment, the beamformer 204 operates as a transmit and receive beamformer. Optionally, the transducer array 38 may include a 2D array with sub-aperture receive beamforming. The beamformer 204 may delay, apodize and/or sum each electrical signal with other electrical signals received from the transducer array 38. The summed signals represent echoes from the ultrasound beams or lines. The summed signals are output from the beamformer 204 to the RF processor 210. The RF processor 210 may generate different data types, e.g. B-mode, color Doppler (velocity/power/variance), tissue Doppler (velocity), and Doppler energy, for multiple scan planes or different scanning patterns. The RF processor 210 gathers the information (e.g. FQ, B-mode, color Doppler, tissue Doppler, and Doppler energy information) related to multiple data slices and stores the data information, which may include time stamp and orientation/rotation information, in the buffer 212.

The ultrasound system 200 also includes a processor 214 (the processor 214 may be embodied as the processor 42 shown in FIG. 1 or may be separate from or coupled thereto) to process the acquired ultrasound information (e.g., RF signal data or IQ data pairs) and prepare frames of ultrasound information for display on a display 216. The processor 214 is adapted to perform one or more processing operations according to a plurality of selectable ultrasound modalities on the acquired ultrasound data. Acquired ultrasound data may be processed and displayed in real-time during a scanning session as the echo signals are received. In another aspect, the ultrasound data may be stored temporarily in the buffer 212 during a scanning session and then processed and displayed in an off-line operation.

The processor 214 is connected to a user interface 218 that may control operation of the processor 214 as explained below in more detail. The display 216 may include one or more monitors that present patient information, including diagnostic ultrasound images to the user for diagnosis and analysis. The buffer 212 and/or a memory 219 may store 2D or 3D data sets of the ultrasound data acquired over time (i.e., 4D data), where such 2D and 3D data sets are accessed to present 2D (and/or 3D images or 4D images). The images may be modified and the display settings of the display 216 may also be manually adjusted using the user interface 218.

FIG. 10 illustrates an embodiment of an Mill system 220 that may be used and, for example, be embodied as the MR system 24. However, in some embodiments, the Mill system 220 may be replaced by the MR system 24. In the exemplary embodiment, the MRI system 220 includes a superconducting magnet 222 formed from magnetic coils that may be supported on a magnet coil support structure. However, in other embodiments, different types of magnets may be used, such as permanent magnets or electromagnets. A vessel 224 (also referred to as a cryostat) surrounds the superconducting magnet 222 and is filled with liquid helium to cool the coils of the superconducting magnet 222. A thermal insulation 226 is provided surrounding the outer surface of the vessel 224 and the inner surface of the superconducting magnet 222. A plurality of magnetic gradient coils 228 are provided within the superconducting magnet 222 and a transmitter, for example, an RF transmit coil 230 is provided within the plurality of magnetic gradient coils 228. In some embodiments the RF transmit coil 230 may be replaced with a transmit and receive coil defining a transmitter and receiver.

The components described above are located within a gantry 232 and generally form an imaging portion 234. It should be noted that although the superconducting magnet 222 is a cylindrical shaped, other shapes of magnets can be used.

A processing portion 240 generally includes a controller 242, a main magnetic field control 244, a gradient field control 246, a display device 248, a transmit-receive (T-R) switch 250, an RF transmitter 252 and a receiver 254. In the exemplary embodiment, motion correction module 260, which may be implemented as a tangible non-transitory computer readable medium, is programmed to perform one or more embodiments as described in more detail herein.

In operation, a patient is inserted into a bore 236 of the MM system 220. The superconducting magnet 222 produces an approximately uniform and static main magnetic field $B_0$ across the bore 236. The strength of the electromagnetic field in the bore 236 and correspondingly in the patient, is controlled by the controller 242 via the main magnetic field control 244, which also controls a supply of energizing current to the superconducting magnet 222.

The magnetic gradient coils 228, which include one or more gradient coil elements, are provided so that a magnetic gradient can be imposed on the magnetic field $B_0$ in the bore 236 within the superconducting magnet 222 in any one or more of three orthogonal directions x, y, and z. The magnetic gradient coils 228 are energized by the gradient field control 246 and are also controlled by the controller 242.

The RF transmit coil 230, which may include a plurality of coils (e.g., resonant surface coils), is arranged to transmit magnetic pulses and/or optionally simultaneously detect MR signals from the patient if receivers, such as receive coil elements are also provided, such as a surface coil (not shown) configured as an RF receive coil. The RF transmit coil 230 and the receive surface coil are selectably interconnected to one of the RF transmitter 252 or the receiver 254, respectively, by the T-R switch 250. The RF transmitter 252 and T-R switch 250 are controlled by the controller 242 such that RF field pulses or signals are generated by the RF transmitter 252 and selectively applied to the patient for excitation of magnetic resonance in the patient.

Following application of the RF pulses, the T-R switch 250 is again actuated to decouple the RF transmit coil 230 from the RF transmitter 252. The detected MR signals are in turn communicated to the controller 242. The detected signals are then utilized to determine electrical properties of the object (e.g., patient) being imaged. The processed signals representative of an image are also transmitted to the display device 248 to provide a visual display of the image.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and/or non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A system comprising:
   one or more patient transports to move a patient into a magnetic resonance (MR) system and to a radiation therapy (RT) system;
   an ultrasound transducer attached to a patient or to one of the one or more patient transports, wherein the ultrasound transducer is electronically steerable, and wherein the ultrasound transducer is configured to acquire four-dimensional (4D) images;
   a controller having a processor configured to:
      simultaneously acquire acquisitions of real-time three-dimensional (3D) MR images over time to produce four-dimensional (4D) MR images, and first real-time 3D ultrasound images over time to produce first 4D ultrasound images, wherein the simultaneous acquisitions are temporally synchronized to a plurality of time points, wherein each of the plurality of time points represents a unique respiration or motion state;
      identify positions of fiducial markers in the first 4D ultrasound image at each of the plurality of time points and link the corresponding 4D MR images of the respective unique respiration or motion state to the positions of the fiducial markers at each of the plurality of time points;
      acquire second real-time 3D ultrasound images over time to produce second 4D ultrasound images during a radiation therapy session, wherein the second 4D ultrasound images is acquired later in time than the first 4D ultrasound images;
      identify current positions of the fiducial markers in the second 4D ultrasound images corresponding to a current respiration or motion state during the radiation therapy session; and
      identify MR images from the 4D MR images corresponding to the current respiratory or motion state of the patient in real-time during the radiation therapy session by using the current positions of the fiducial markers without performing a spatial registration between any of second 4D ultrasound images and any of the 4D MR images.

2. The system of claim 1, wherein the 4D MR images are linked to a list of positions of the fiducial markers, wherein the list of positions is represented by:

$$R_1(t):U(\vec{r},t) \rightarrow M(\vec{r},t)$$

wherein $R_1(t)$ represents a collection of the positions of fiducial markers identified in the first 4D ultrasound images at time, t, corresponding to a respective 4D MR image;

wherein $U(\vec{r}, t)$ represents the 4D ultrasound images; and wherein $M(\vec{r}, t)$ represents the 4D MR images.

3. The system of claim 2, wherein the collection is a set of unique identifiers associated with different respiration or motion states as determined by the positions of the fiducial markers.

4. The system of claim 1, wherein the fiducial markers include one or more anatomical markers.

5. The system of claim 1, wherein 4D MR images and the 4D ultrasound images are acquired asynchronously.

6. An integrated radiation therapy (RT) system comprising:
- one or more patient transports to move a patient into a magnetic resonance (MR) system and to a radiation therapy (RT) system;
- an ultrasound transducer attached to a patient or to one of the one or more patient transports, wherein the ultrasound transducer is electronically steerable;
- a controller having a processor configured to:
  - simultaneously acquire, during a pre-treatment phase, one or more MR images and one or more first ultrasound images;
  - temporally synchronize, during the pre-treatment phase, the one or more MR images and the one or more first ultrasound images to a plurality of time points, wherein each of the plurality of time points represents a unique respiration or motion state;
  - acquire, during a treatment phase, one or more second ultrasound images, wherein the treatment phase occurs after the pre-treatment phase;
  - identify current positions of fiducial markers in the one or more second ultrasound images corresponding to a current respiration or motion state during the treatment phase; and
  - identify images from the one or more MR images corresponding to the current respiratory or motion state of the patient in real-time during the treatment phase without performing a spatial registration between any of the one or more second ultrasound images and the one or more MR images wherein the processor is further configured to: identify positions of fiducial markers representing a specific respiration or motion state from the first one or more ultrasound images at each of the plurality of time points in the pre-treatment phase; and link the corresponding, temporally synchronized, one or more MR images of the respective specific respiration or motion state to the positions of the fiducial markers.

7. The integrated RT system of claim 6, wherein the processor is configured to identify the one or more MR images corresponding to the current respiratory or motion state of the patient by using index matching.

8. The integrated RT system of claim 7, wherein the index matching is performed by matching positional variation of the one more fiducial markers due to specific respiration or motion state to a set of number indices, and using the set of number indices to identify the one of more MR images corresponding to the current respiratory or motion state of the patient in real-time.

9. The integrated RT system of claim 6, wherein images from the one or more MR images corresponding to the current respiratory or motion state of the patient in real-time during the treatment phase are identified by matching current positions of fiducial markers during the the treatment phase with the positions of fiducial markers in the pre-treatment phase and matching the corresponding MR images in the pre-treament phase.

* * * * *